United States Patent [19]

Tschopp et al.

[11] Patent Number: 4,661,440
[45] Date of Patent: Apr. 28, 1987

[54] PROCESS FOR STABILIZING PHOTOGRAPHIC MATERIAL CONTAINING MAGENTA COUPLER

[75] Inventors: Paul Tschopp, Düdingen; David G. Leppard, Marly, both of Switzerland

[73] Assignee: Ciba-Geigy AG, Basel, Switzerland

[21] Appl. No.: 795,859

[22] Filed: Nov. 7, 1985

[30] Foreign Application Priority Data

Nov. 7, 1984 [CH] Switzerland .......................... 5359/84

[51] Int. Cl.$^4$ ................................................ G03C 1/40
[52] U.S. Cl. .................................... 430/512; 430/372; 430/551; 430/610; 430/931
[58] Field of Search ............... 430/372, 551, 610, 512, 430/931

[56] References Cited

FOREIGN PATENT DOCUMENTS 48-32728 10/1973 Japan .
52-082219 12/1975 Japan .
53-108428  3/1977 Japan .
57-204036  6/1981 Japan .

OTHER PUBLICATIONS

Tuite, J. Appl. Photogr. Eng. 5, 200, 1979.

*Primary Examiner*—Richard L. Schilling
*Attorney, Agent, or Firm*—Wenderoth, Lind & Ponack

[57] ABSTRACT

Photographic material containing magenta coupler is stabilized by incorporating a dibenzoxaphosphorin of the formula

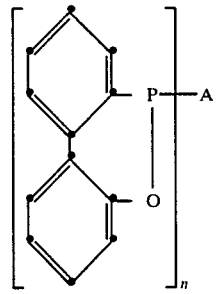

into the emulsion layer containing the coupler or into an adjoining colloid layer. The yellowing on dark storage of such material is substantially reduced as a result.

The symbols A and n are defined in claim 1.

11 Claims, No Drawings

PROCESS FOR STABILIZING PHOTOGRAPHIC MATERIAL CONTAINING MAGENTA COUPLER

The present invention relates to a process for stabilising photographic material containing magenta coupler by incorporating a dibenzoxaphosphorin into the coupler-containing emulsion layer or into an adjoining colloid layer.

A big problem with the dark storage of photographic materials which contain at least one magenta coupler is that owing to the decomposition of this coupler, yellowing takes place (see R. J. Tuite: "Image Stability in Color Photography", J. Appl. Photogr. Eng. 5, 200, 1979). Furthermore, this decomposition leads to reduced dye formation in the coupling reaction and consequently to altered reproduction of different hues.

Attempts have therefore already been made to solve this problem. For instance, Japanese Offenlegungsschrift No. 52/082,219 describes a chromogenic colour-photographic material in which said yellowing is reduced by the presence of certain polyvinylimidazoles. Japanese Offenlegungsschrift No. 53/108,428 discloses a colour-photographic material which contains for this purpose substituted 4-hydroxyphosphoranilides; Japanese Offenlegungsschrift No. 57/204,036 discloses such a material which contains pyrocatechol dialkyl ethers; and Japanese Auslegeschrift No. 48-32,728 discloses such a material containing alkyl phosphites and/or aryl phosphites.

It has nonetheless not been possible to date to solve the problem in a satisfactory way, since these compounds have only little activity. It has now been found, surprisingly, that certain dibenzoxaphosphorins largely prevent the yellowing which is caused, on dark storage, by the magenta coupler.

The present invention accordingly provides a process for stabilising photographic material containing magenta coupler, which comprises incorporating into the emulsion layer containing the magenta coupler or into an adjoining colloid layer at least one compound of the formula I

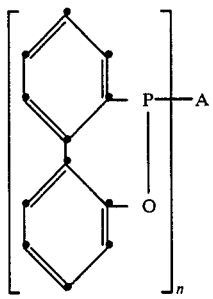
(I)

in which n is the number 1 or 2 and
A, if n is 1, is a group of the formula II

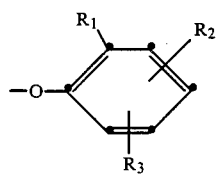
(II)

in which $R_1$ is $C_1$-$C_{18}$-alkyl, $C_5$-$C_6$-cycloalkyl, Cl, Br, CN, $C_7$-$C_{21}$-aralkyl or a group of the formula III

(III)

in which X is $C_2$-$C_8$-alkylene and Y is a —$OR_4$, —$N(R_5)(R_6)$, $C_1$-$C_4$-alkyl, the residue

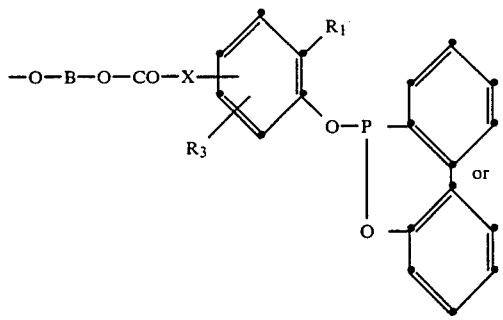

or

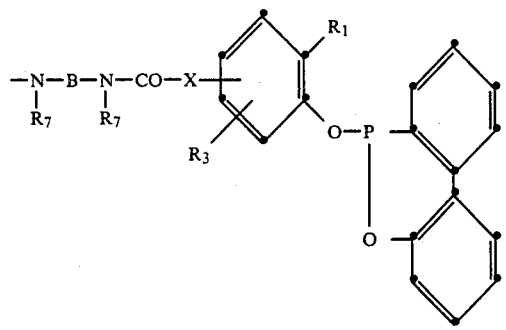

wherein B is $C_1$-$C_{18}$-alkylene which is uninterrupted or interrupted one or more times by —O— or —S— or is a group of the formula

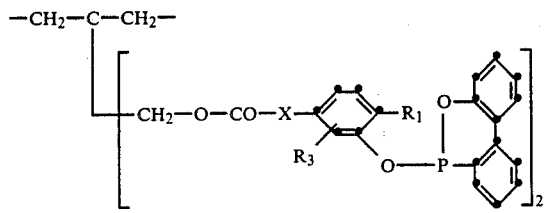

$R_2$ is hydrogen, $R_1$ or a —$OR_7$ group, $R_3$ is hydrogen or $R_1$, $R_4$ is $C_1$-$C_{18}$-alkyl which is uninterrupted or interrupted one or more times by —O— or is a polyethylene glycol radical, phenyl, substituted phenyl or benzyl, $R_5$ and $R_6$, independently of each other, are hydrogen, $C_1$-$C_{18}$-alkyl, phenyl, benzyl or a —$(CH_2)_m$—O—$R_8$ group, $R_7$ is hydrogen or $C_1$-$C_4$-alkyl, $R_8$ is $C_1$-$C_{18}$-alkyl and m is a number between 1 and 4, or $R_2$ and $R_3$ together are $C_3$-$C_8$-alkylene or a group

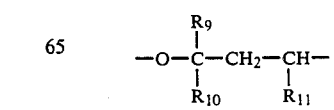

in which $R_9$, $R_{10}$ and $R_{11}$ independently of one another are each $C_1$-$C_4$-alkyl, or A, if n is 2, is a group of the formula IV

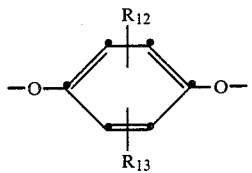 (IV)

in which $R_{12}$ and $R_{13}$, independently of each other, are each $C_1$-$C_{18}$-alkyl or a group of the formula III or A is a group of the formula V

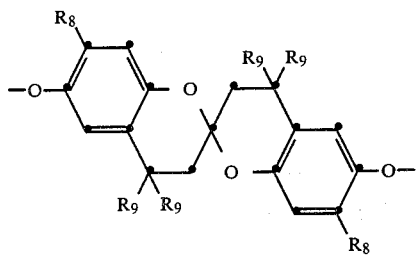 (V)

in which $R_8$ and $R_9$ are as defined above.

In the $C_1$-$C_{18}$-alkyl substituents can be straight-chain or branched alkyl, for example, methyl, ethyl, propyl, i-propyl, butyl, i-butyl, tert.-butyl, amyl, 1,1-dimethylpropyl, 1,1,3,3-tetramethylbutyl, 1-methylpentyl, hexyl, heptyl, n-octyl, 2-ethylhexyl, n-nonyl, isononyl, decyl, tert.-decyl, undecyl, dodecyl, tetradecyl, hexadecyl, octadecyl. Alkyls $R_1$, $R_2$, $R_{12}$ and $R_{13}$ are preferably branched alkyl having 4 to 8 carbon atoms and in particular tert.-butyl or 1,1,3,3-tetramethylbutyl. $R_4$ is preferably straight-chain alkyl having 4 to 12 carbon atoms and in particular n-hexyl.

$C_1$-$C_4$-alkyls $R_7$, $R_9$, $R_{10}$ and $R_{11}$ are for example methyl, ethyl, propyl, i-propyl, butyl, i-butyl or tert.-butyl. They are preferably methyl.

In the $C_5$-$C_6$-cycloalkyl substituents are cyclopentyl and in particular cyclohexyl.

Any $C_7$-$C_{21}$-aralkyl substituents are for example benzyl which is unsubstituted or monosubstituted or disubstituted in the phenyl nucleus by methyl, ethyl, propyl, i-propyl, n-butyl, i-butyl or tert.-butyl and are in particular α,α-dimethylbenzyl.

$C_3$-$C_8$-alkylene $R_2$ and $R_3$ together is for example trimethylene or tetramethylene and in particular the —C(CH$_3$)$_2$—CH$_2$—C(CH$_3$)$_2$— group.

An $R_2$ and $R_3$ together group of the formula

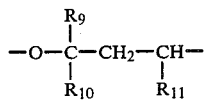

is in particular the group

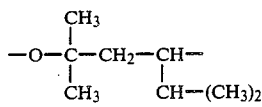

A $C_2$-$C_8$-alkylene X is for example ethylene, propylene, trimethylene, hexamethylene and in particular the —C(CH$_3$)$_2$—(CH$_2$)$_3$— group where the dimethyl-substituted carbon atom is bonded to the phenyl nucleus.

B is for example methylene, ethylene, 1,2-propylene, trimethylene, hexamethylene, dodecamethylene, octadecamethylene, 1,2-hexylene, a —CH$_2$CH$_2$—O—$_2$CH$_2$CH$_2$— or —CH$_2$CH$_2$—S—CH$_2$CH$_2$— group and in particular ethylene, trimethylene, tetramethylene, pentamethylene or hexamethylene.

Substituted phenyl $R_4$ is for example phenyl which is substituted by one or more $C_1$-$C_{12}$-alkoxy and/or $C_1$-$C_{12}$-alkyl groups, by one halogen, for example chloro or bromo, phenyl, aralkyl, for example benzyl, or a —(CH$_2$—)$_3$ group which is attached to two adjoining C atoms of the phenyl nucleus. Examples of $R_4$ as substituted phenyl are 4-methoxyphenyl, 4-ethoxyphenyl, 3,5-dimethylphenyl, 4-benzylphenyl, 4-n-dodecylphenyl or 4-chlorophenyl.

Dibenzoxaphosphorins of preferred use in the process according to the invention are those of formula I in which A, if n is 1, is a group of the formula II

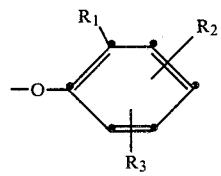 (II)

in which $R_1$ is $C_1$-$C_{18}$-alkyl, $C_5$-$C_6$-cycloalkyl, Cl, Br, CN, $C_7$-$C_{21}$-aralkyl or a group of the formula III

 (III)

in which X is $C_2$-$C_8$-alkylene and Y is a —OR$_4$ or —N(R$_5$)(R$_6$) group, $R_2$ is hydrogen, $R_1$ or a —OR$_7$ group, $R_3$ is hydrogen or $R_1$, $R_4$ is $C_1$-$C_{18}$-alkyl which is uninterrupted or interrupted one or more times by —O— or is a polyethylene glycol radical, phenyl or benzyl, $R_5$ and $R_6$, independently of each other, are hydrogen, $C_1$-$C_{18}$-alkyl, phenyl, benzyl or a —(CH$_2$)$_m$—O—R$_8$ group, $R_7$ is hydrogen or $C_1$-$C_4$-alkyl, $R_8$ is $C_1$-$C_{18}$-alkyl and m is a number between 1 and 4, or $R_2$ and $R_3$ together are $C_3$-$C_8$-alkylene or a group

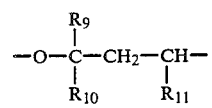

in which $R_9$, $R_{10}$ and $R_{11}$ independently of one another are each $C_1$-$C_4$-alkyl, or A, if n is 2, is a group of the formula IV

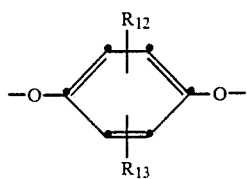

in which $R_{12}$ and $R_{13}$, independently of each other, are each $C_1$-$C_{18}$-alkyl or a group of the formula III or
A is a group of the formula V

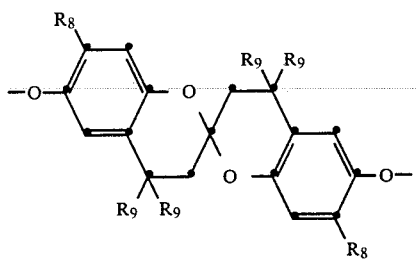

in which $R_8$ and $R_9$ are as defined above.

Dibenzoxaphosphorins of particular interest for use in the process according to the invention are those of the formula I in which A, if n is 1, is a group of the formula II in which $R_1$ and $R_2$, independently of each other, are each hydrogen, $C_1$-$C_{18}$-alkyl or $C_7$-$C_{21}$-aralkyl and $R_3$ is hydrogen or $R_2$ and $R_3$ together are $C_2$-$C_8$-alkylene, or A, if n is 2, is a group of the formula IV in which $R_{12}$ and $R_{13}$ are each $C_1$-$C_{18}$-alkyl or a —X—C(O)OR$_4$ group in which X and $R_4$ are as defined above.

Dibenzoxaphosphorins of preferred use in the process according to the invention are those of the formula I in which A, if n is 1, is a group of the formula VI

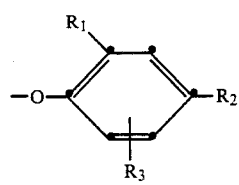

in which $R_1$ and $R_2$ are each branched $C_4$-$C_8$-alkyl or α,α-dimethylbenzyl and $R_3$ is hydrogen or $R_2$ and $R_3$ together are the —C(CH$_3$)$_2$—CH$_2$—C(CH$_3$)$_2$— group, or A, if n is 2, is a group of the formula VII

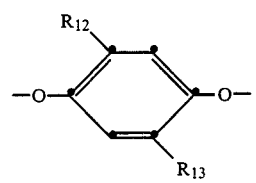

in which $R_{12}$ and $R_{13}$ are each branched alkyl or a group
of the formula VIII $$-C(CH_3)_2(CH_2)_3COOR_4 \qquad (VIII)$$

in which $R_4$ is $C_1$-$C_{18}$-alkyl.

Dibenzoxaphosphorins of particularly preferred use in the process according to the invention are those of the formula I in which A, if n is 1, is a group of formula VI in which $R_1$ and $R_2$ are each tert.-butyl, 1,1,3,3-tetramethylbutyl or α,α-dimethylbenzyl and $R_3$ is hydrogen or $R_2$ and $R_3$ together are a —C(CH$_3$)$_2$—CH$_2$—C(CH$_3$)$_2$— group, or A, if n is 2, is a group of the formula VII in which $R_{12}$ and $R_{13}$ are each tert.-butyl, 1,1,3,3-tetramethylbutyl or a group of the formula VIII in which $R_4$ is $C_1$-$C_{10}$-alkyl.

The compounds of the formula I are used in an amount of 1–400 mol %, preferably 20–100 mol %, based on the magenta coupler.

Non-limiting examples of compounds of the formula I are the compounds of the following formulae:

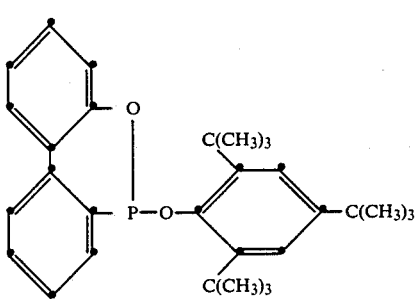

stabiliser 1

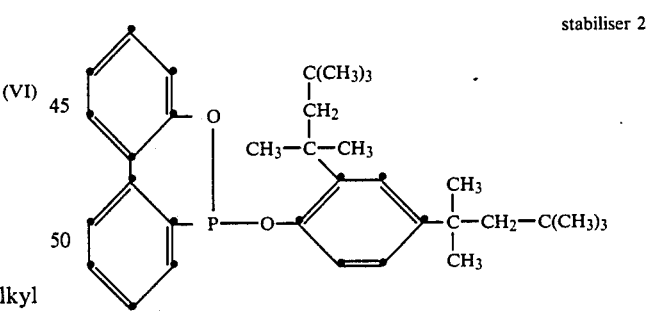

stabiliser 2

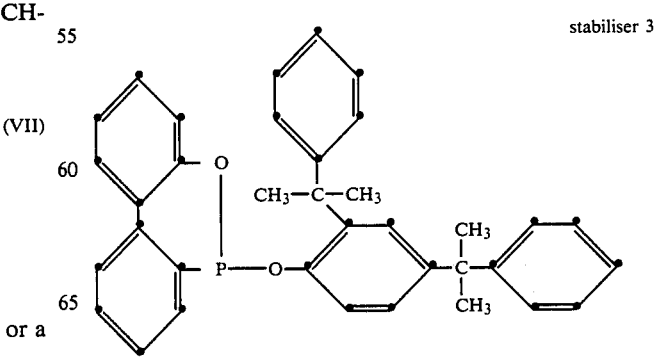

stabiliser 3 stabiliser 4
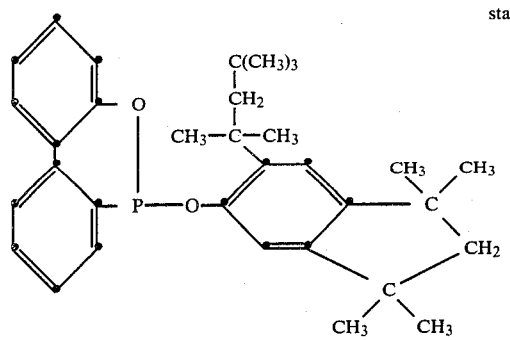
stabiliser 8
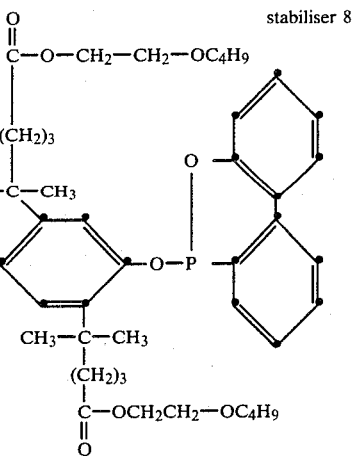
stabiliser 5
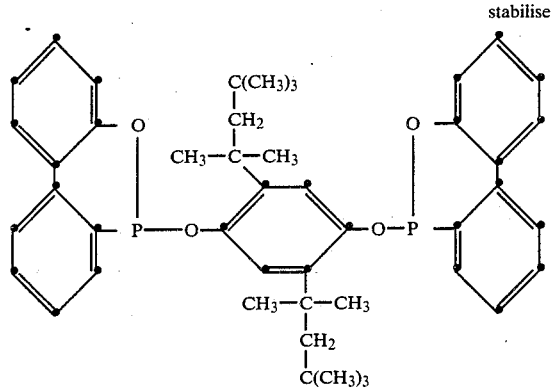
stabiliser 9
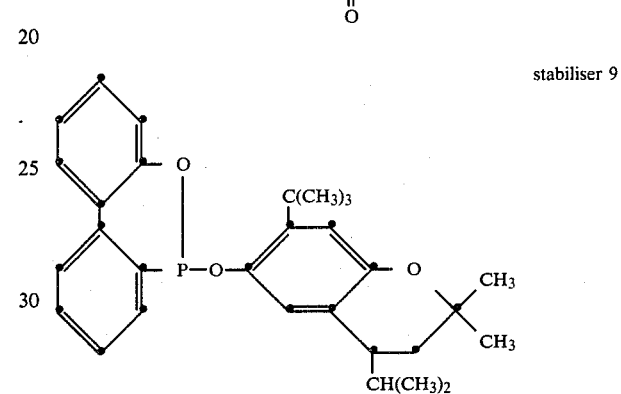
stabiliser 6
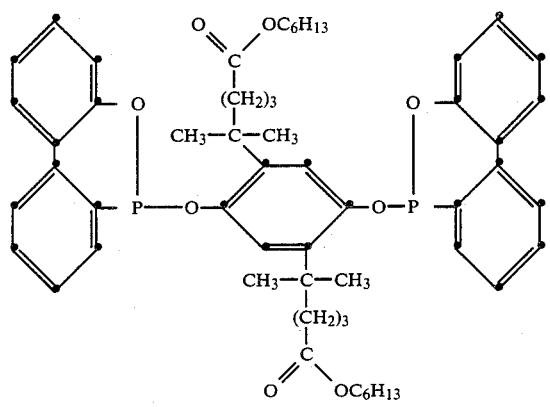
Further examples:
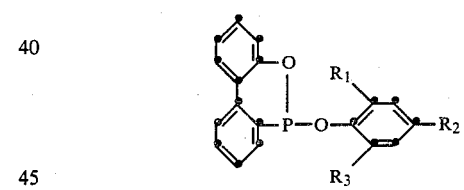
| Stabiliser | $R_1$ | $R_2$ | $R_3$ |
|---|---|---|---|
| 10 | $-CH(CH_3)_2$ | $-C(CH_3)_3$ | $-CH(CH_3)_2$ |
| 11 | $-C(CH_3)_3$ | $-CH(CH_3)_2$ | $-C(CH_3)_3$ |
stabiliser 7
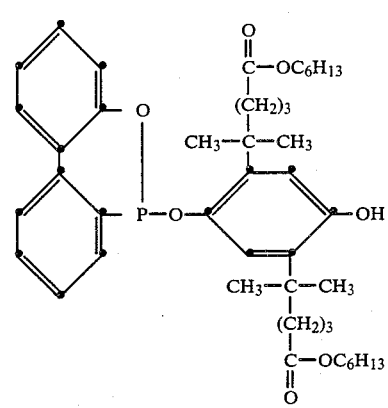
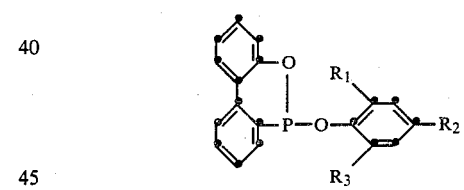
| Stabiliser | B |
|---|---|
| 12 | $-(CH_2)_6-$ |
| 13 | $-(CH_2CH_2-O)_2CH_2CH_2-$ |
| 14 | $-CH_2CH_2-S-CH_2CH_2-$ | stabiliser 15

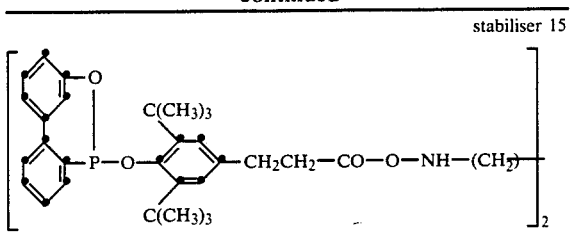

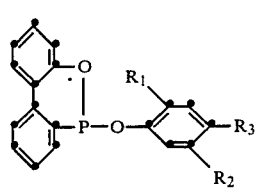

| Sta-bi-liser | R₁ | R₂ | R₃ |
|---|---|---|---|
| 16 | —C(CH₃)₂(CH₂)₃COOCH₃ | OH | as R₁ |
| 17 | —C(CH₃)₃ | | —C(CH₃)₂—CH₂—C(CH₃)₂— | stabiliser 18

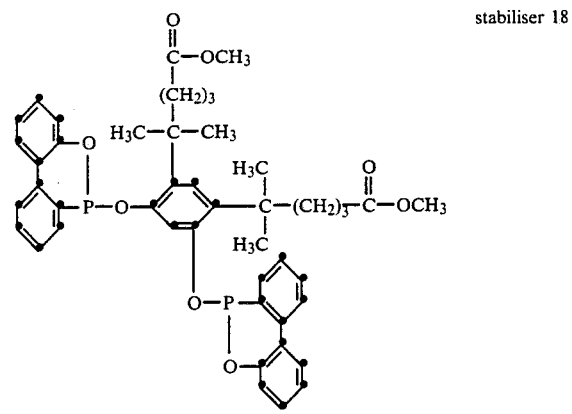

Compounds of the formula I in which

A, if n is 1, is a group of the formula II in which R₁, R₂ and R₃, independently of one another, are each $C_1$-$C_8$-alkyl, α,α-dimethylbenzyl or a group of the formula III, R₂ can additionally be methoxy or ethoxy and R₃ can additionally be hydrogen, with the proviso that at least one of R₁, R₂ and R₃ is a group of the formula III, or A, if n is 2, is a group of the formula VII in which R₁₂ and R₁₃ are each a group of the formula III, are novel and form a further part of the subject-matter of this invention. They can be prepared analogously to conventional methods, for example by reacting a phenol of the formula IX

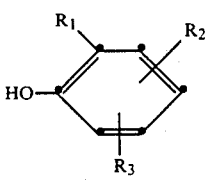 (IX)

or a hydroquinone of the formula X

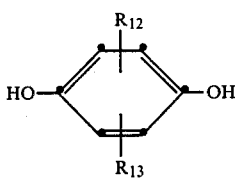 (X)

with possibly one or two mol respectively of 6-chlorodibenz[c,e][1,2]-oxaphosphorin as described for example in Example 1.

Non-limiting examples of further novel compounds of the formula I are the following compounds:

compounds of the formula I in which n is 1

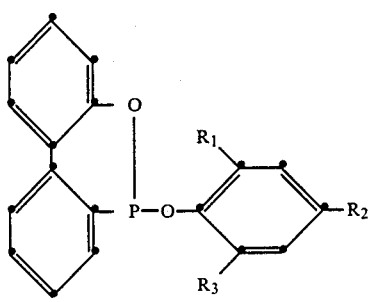

| R₁ | R₂ | R₃ |
|---|---|---|
| —C(CH₃)₂—(CH₂)₃—COOCH₃ | —C(CH₃)₃—(CH₂)₃—COOCH₃ | —C(CH₃)₂—(CH₂)₃—COOCH₃ |
| —C(CH₃)₂—(CH₂)₃—COOCH₃ | —CH₃ | —C(CH₃)₂—(CH₂)₃—COOCH₃ |
| —C(CH₃)₃ | —C(CH₃)₂—(CH₂)₃—COOCH₃ | —CH₃ |
| —C(CH₃)₂—(CH₂)₃—COOCH₃ | —C(CH₃)₃ | H |
| —C(CH₃)₂—(CH₂)₃—COOCH₃ | —C(CH₃)₃ | —C(CH₃)₃ |

Compounds of the formula I, which are used with particular preference in the process according to the invention, are stabilisers 2, 6 and 7. Except for stabilisers 6 to 9 and 12 to 15, which are novel, all the compounds to be used according to the invention are known.

Compounds of the formula I in which n is 2

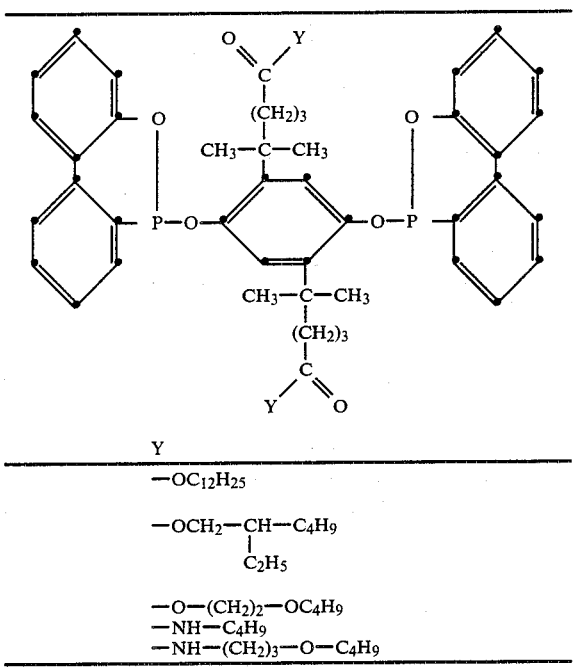

| Y |
|---|
| $-OC_{12}H_{25}$ |
| $-OCH_2-CH-C_4H_9$<br>      $\|$<br>     $C_2H_5$ |
| $-O-(CH_2)_2-OC_4H_9$ |
| $-NH-C_4H_9$ |
| $-NH-(CH_2)_3-O-C_4H_9$ |

The compounds of the formula I, like indeed colour couplers, can be incorporated in known manner into photographic layers, for example into silver halide emulsions which contain gelatin and/or other binders. They find utility for example in silver bromide, silver chloride or silver iodide emulsions or in emulsions which contain mixtures of silver halides, such as silver bromide/iodide or silver chloride/bromide emulsions. The emulsions can be chemically sensitised and additionally contain customary organic stabilisers or mixtures thereof such as hindered amines, phenolic components such as hindered phenols, alkoxyphenols, aryloxyphenols, hydroxycoumarans, hydroxychromans or dihydroxyspirochromans, disulphoneamidophenols or substituted hydroquinones (as described for example in German Offenlegungsschrift No. 2,417,867 and European Patent Application No. 69,070), substituted hydroquinone monoethers (as described for example in European Patent Application No. 98,241) and substituted hydroquinone diethers (as described for example in German Offenlegungsschrift No. 2,839,434), synergistic effects being possible, and also UV absorbers, fluoroescent brightening agents and photographically active compounds, and also antifogging agents, compounds which can release photochemically active products such as DIR compounds, and customary plasticisers, such as glycerol. The colour couplers and dibenzoxaphosphorins are in the rule soluble in solvents of high boiling-points. Such solvents have a boiling-point above 150° C. and their molecular weight is between 100 and 1000, as for example organic amides, carbonates, esters, cetons and urea derivatives. Solvents of preferred use are di-n-butyl phthalate, di-octyl phthalate, tricesyl phosphate, trioctyl phosphate, di-iso-octyl azelaic ester, di-n-butyl sebacate, n-nonylphenol or a mixture thereof. The emulsions can also be cured with curing agents customary for gelatin. Finally, the emulsions can contain also customary coating assistants. The emulsions can be applied to customary support materials for photographic image material. If desired, it is possible to use a mixture of different colloids for dispersing the silver halides. In addition to the magenta coupler the emulsions can also contain other couplers which alone or in mixtures produce dyes during the development, for example yellow, cyano or black dyes.

To develop the image material for colour photography it is possible to use customary development baths. These baths generally contain a development substance of the p-phenyldiamine type; a development-inhibitor, such as potassium bromide; an antioxidant, such as a salt of sulphurous acid, for example sodium sulphite and/or hydroxylamine; and a base, for example an alkali metal hydroxide or alkali metal carbonate. The development baths can also contain customary antifogging agents, complexing agents, wetting agents, fluorescent brightening agents and the like.

Appropriate uses have been described for example in U.S. Pat. Nos. 2,304,939, 2,304,940, 2,322,027, 2,284,879, 2,801,170, 2,801,171, 2,749,360 and 2,825,382.

The photographic material to be stabilised according to the invention contains the customarily used magenta couplers as described, for example, in The Theory of the Photographic Process, 4th edition, Macmillan, New York, N.Y., pages 356–358 and in U.S. Pat. No. 3 676 137, for example those of the pyrazolone type, in particular 1-(substituted phenyl)-3-anilino-, -3-benzanilido- and -3-ureido-pyrazolin-5-one. These couplers can be biequivalent or tetraequivalent couplers.

Preferably used are magenta couplers of the formula

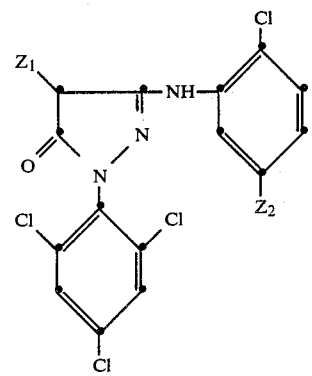

in which $Z_1$ is hydrogen or a group which stays free during development, such as

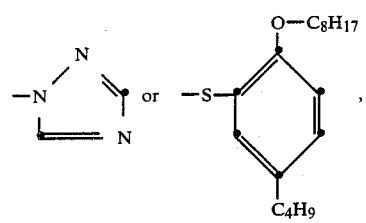

and $Z_2$ is a group

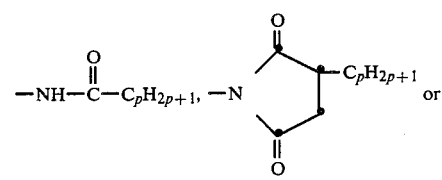

-continued

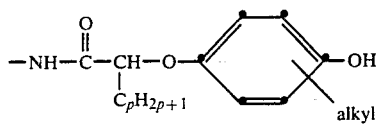

in which p is a number between 1 and 18.

The following examples illustrate the invention.

EXAMPLE 1

5.0 g of 2,5-bis-(5-n-hexyloxycarbonyl-2-methylpent-2-yl)-hydroquinone are dissolved in 150 ml of triethylamine and 5.1 g of 6-chlorodibenz-[c,e][1,2]-oxaphosphorin are added. The reaction mixture is stirred at 80° C. for 4 hours, is cooled down to room temperature and is filtered. The triethylamine is distilled off under reduced pressure, and the remaining oil is dissolved in 60 ml of petroleum ether. This solution is cooled down to 0° C. and is filtered. The filter residue is washed with cold petroleum ether and is dried. This gives 3.5 g of 1,4-bis-(dibenz[c,e][1,2]-oxaphosphorin-6-yloxy)-2,5-bis-(5'-n-hexyloxycarbonyl-2'-methylpent-2'-yl)-benzene having a melting point of 85°–90° C. (Stabiliser 6).

EXAMPLE 2

0.145 g of the magenta coupler of the formula

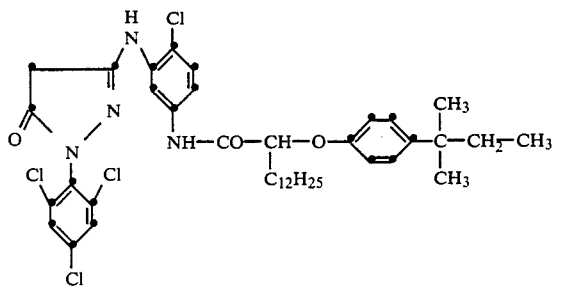

and 0.05 g of one of the stabilisers which are specified in the table below for use according to the invention are dissolved in 5 ml of a mixture of tricresyl phosphate/ethyl acetate (1.5 g in 100 ml). 1 ml of this solution is emulsified with 9 ml of a 2.3% gelatin solution which contains 0.04% by weight of wetting agent of the formula

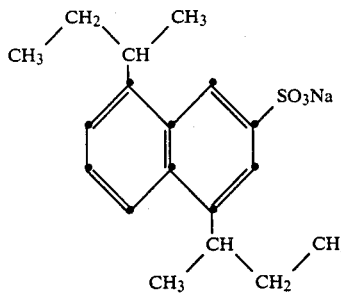

for 3 minutes in an ice-water bath with 75 watt power ultrasound. 5 ml of this emulsion are mixed with 2 ml of a silver bromide emulsion which contains 71 g of gelatin and 55 g of silver per 1 kg of emulsion and with 1 ml of an 0.7% aqueous solution of the curing agent of the formula

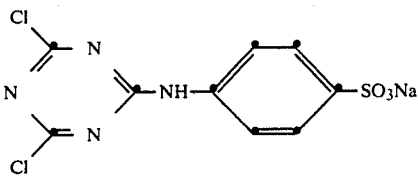

and the mixture is poured at pH 6.5 onto a plastic-coated sheet of paper 13×18 cm in size.

After solidification, the cast is dried at room temperature with circulating air in a drying cabinet. After 7 days this manual cast is exposed with 33 lux.sec behind a step wedge and is then processed using Kodak's Ektaprint 2 ® process.

The magenta wedges thus obtained are stored for 28 days in a conditioning cabinet at 60° C. and 60% relative humidity. By means of measurements at the start and at the end of the treatment a TR 924 ® Macbeth densitometer is used to determine conditioned yellowing in the blue channel in accordance with the formula Conditioned yellowing = $D_{min}(blue)_{28\ days} - D_{min}(blue)_{0\ days}$ (C.Y.)

The results are shown in the table below.

| Stabiliser | Conditioned yellowing (C.Y.) $D_{min}(blue)_{28} - D_{min}(blue)_0$ |
|---|---|
| None | 0.15 |
| Stabiliser 2 | 0.07 |
| Stabiliser 3 | 0.06 |
| Stabiliser 4 | 0.06 |
| Stabiliser 5 | 0.05 |
| Stabiliser 6 | 0.06 |
| Stabiliser 7 | 0.11 |
| Stabiliser 8 | 0.06 |
| Stabiliser 9 | 0.06 |

EXAMPLE 3

0.145 g of the magenta coupler of the formula

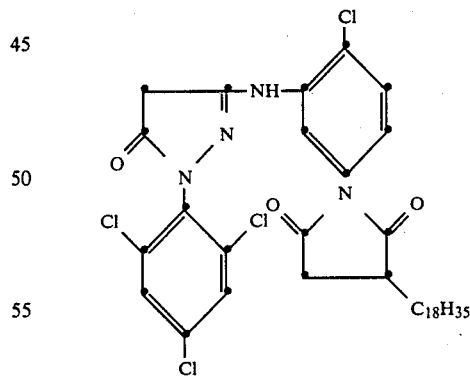

and 0.05 g of Stabiliser 6 are treated as in Example 2. The conditioned yellowing is shown in the table below.

| Stabiliser | Conditioned yellowing (C.Y.) $D_{min}(blue)_{28} - D_{min}(blue)_0$ |
|---|---|
| None | 0.20 |
| Stabiliser 6 | 0.10 |

EXAMPLE 4

0.145 g of the magenta coupler of the formula

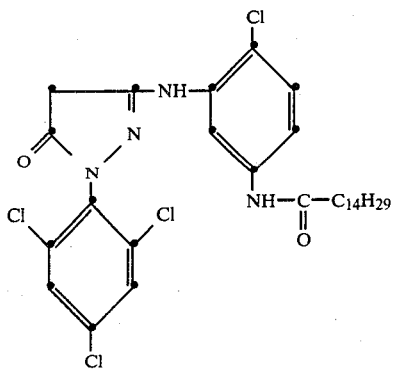

and 0.05 g of Stabiliser 6 are treated as in Example 2. The conditioned yellowing is shown in the table below.

| Stabiliser | Conditioned yellowing (C.Y.) $D_{min}$ (blue)$_{28}$ − $D_{min}$ (blue)$_0$ |
|---|---|
| None | 0.21 |
| Stabiliser 6 | 0.15 |

In the following examples, an additional light-stabiliser is used together with Stabiliser 6 for the magenta coupler.

EXAMPLE 5

0.145 g of the magenta coupler of the formula

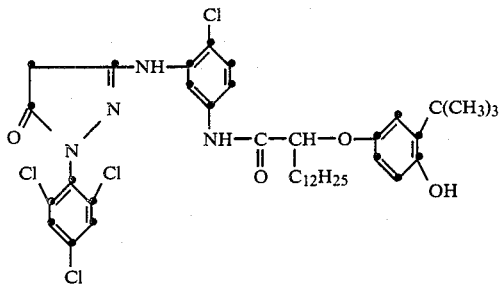

and 0.05 g of Stabiliser 6 or a light-stabiliser for the magenta coupler (short MFLS*) of the formula

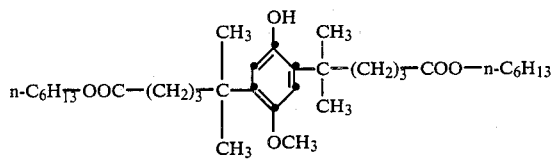

or a mixture of Stabiliser 6 and MFLS is treated like in Example 2.

*MFLS = Magenta-Farbstoff-Lichtstabilisator

One part of the magenta wedges thus obtained are stored for 28 days in a conditioning cabinet at 70° C. and 60% relative humidity and then the conditioned yellowing is determined as described in Example 2.

The other part of the magenta wedges is irradiated at 30 kJ/cm² behind an UV-filter, in an Atlas Weather-Ometer, type C: 35 W, (2C-filter of Kodak). By means of measurements of the density at the start and at the end of the treatment is the Atlas yellowing (A.Y.) determined according to the formula Atlas yellowing $(A.Y.) = D_{min}(\text{blue})_{30\ kJ/cm2} - D_{min}(\text{blue})_{0\ kJ/cm2}$ The loss of dye is determined by measuring the loss of density in the green channel relative to the density before the treatment, which is D=1.0 (given in percentage). All determinations of the density are carried out in the apparatus described in Example 2.

The results are shown in the table below.

| Stabiliser | C.Y. | A.Y. | Loss of dye (%) |
|---|---|---|---|
| None | 0.23 | 0.20 | 26 |
| MFLS | 0.25 | 0.17 | 16 |
| Stabiliser 6 | 0.19 | 0.11 | 27 |
| MFLS + Stabiliser 6 (1:1) | 0.18 | 0.11 | 19 |
| MFLS + Stabiliser 6 (1:2) | 0.17 | 0.10 | 21 |

EXAMPLE 6

0.077 g of the magenta coupler of the formula

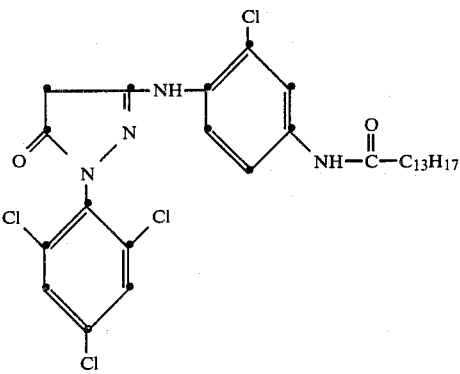

and 0.023 g of Stabiliser 6 or MFLS of Example 5, or 0.046 g of a mixture of the above-mentioned two stabilisers are treated as in Example 5.

The results are shown in the table below.

| Stabiliser | C.Y. | A.Y. | Loss of dye (%) |
|---|---|---|---|
| None | 0.13 | 0.15 | 75 |
| MFLS | 0.22 | 0.11 | 32 |
| Stabiliser 6 | 0.09 | 0.11 | 66 |
| MFLS + Stabiliser 6 (1:1) | 0.11 | 0.07 | 36 |

What is claimed is:

1. A process for stabilising photographic silver halide material containing magenta coupler, which comprises incorporating into the silver halide emulsion layer containing the magenta coupler or into an adjoining colloid layer at least one compound of the formula I

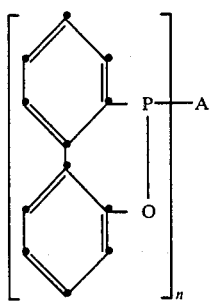

in which n is the number 1 or 2 and
A, if n is 1, is a group of the formula II

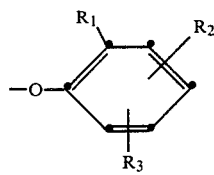

in which $R_1$ is $C_1$-$C_{18}$-alkyl, $C_5$-$C_6$-cycloalkyl, Cl, Br, CN, $C_7$-$C_{21}$-aralkyl or a group of the formula III

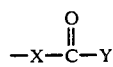

in which X is $C_2$-$C_8$-alkylene and Y is a —$OR_4$, —$N(R_5)(R_6)$, $C_1$-$C_4$-alkyl, the residue

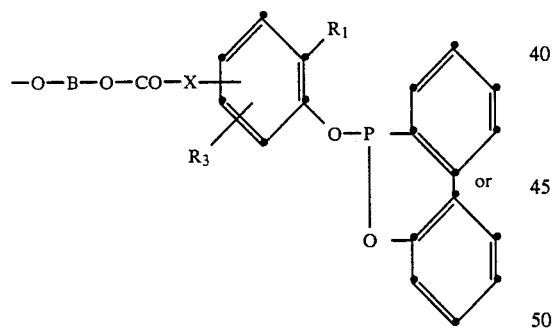

or

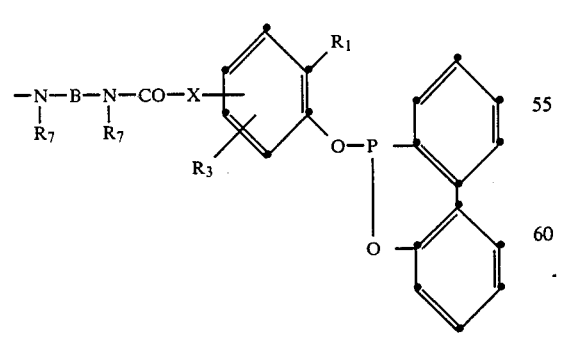

wherein B is $C_1$-$C_{18}$-alkylene which is uninterrupted or interrupted one or more times by —O— or —S— or is a group of the formula

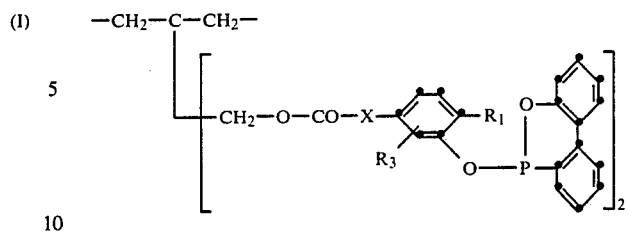

$R_2$ is hydrogen, $R_1$ or a —$OR_7$ group, $R_3$ is hydrogen or $R_1$, $R_4$ is $C_1$-$C_{18}$-alkyl which is uninterrupted or interrupted one or more times by —O— or is a polyethylene glycol radical, phenyl, substituted phenyl or benzyl, $R_5$ and $R_6$, independently of each other, are hydrogen, $C_1$-$C_{18}$-alkyl, phenyl, benzyl, or a —$(CH_2)_m$—O—$R_8$ group, $R_7$ is hydrogen or $C_1$-$C_4$-alkyl, $R_8$ is $C_1$-$C_{18}$-alkyl and m is a number between 1 and 4, or $R_2$ and $R_3$ together are $C_3$-$C_8$-alkylene or a group

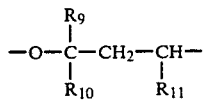

in which $R_9$, $R_{10}$, $R_{11}$ independently of one another are each $C_1$-$C_4$-alkyl, or
A, if n is 2, is a group of the formula IV

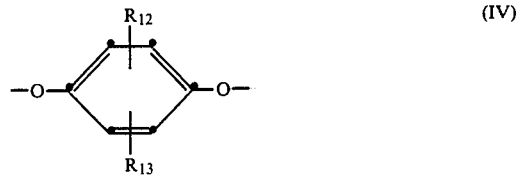

in which $R_{12}$ and $R_{13}$, independently of one another, are each $C_1$-$C_{18}$-alkyl or a group of the formula III or
A is a group of the formula V

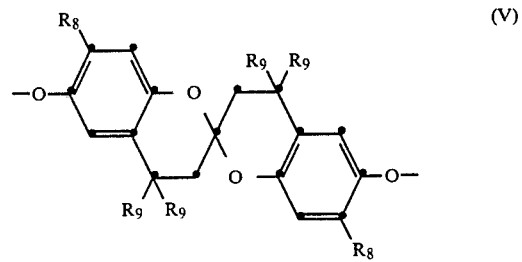

in which $R_8$ and $R_9$ are as defined above.

2. A process according to claim 1, wherein the compound used has the formula I in which A, if n is 1, is a group of the formula II

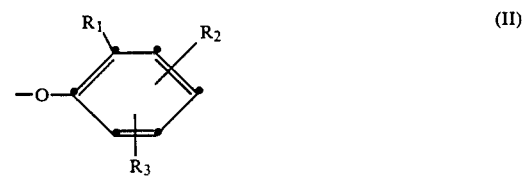

in which $R_1$ is $C_1$-$C_{18}$-alkyl, $C_5$-$C_6$-cycloalkyl, Cl, Br, CN, $C_7$-$C_{21}$-aralkyl or a group of the formula III

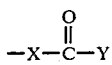

in which X is $C_2$-$C_8$-alkylene and Y is a —$OR_4$ or —$N(R_5)(R_6)$ group, $R_2$ is hydrogen, $R_1$ or a —$OR_7$ group, $R_3$ is hydrogen or $R_1$, $R_4$ is $C_1$-$C_{18}$-alkyl which is uninterrupted or interrupted one or more times by —O— or is a polyethylene glycol radical, phenyl or benzyl, $R_5$ and $R_6$, independently of each other, are hydrogen, $C_1$-$C_{18}$-alkyl, phenyl, benzyl, or a —$(CH_2)_m$—O—$R_8$ group, $R_7$ is hydrogen or $C_1$-$C_4$-alkyl, $R_8$ is $C_1$-$C_{18}$-alkyl and m is a number between 1 and 4, or $R_2$ and $R_3$ together are $C_3$-$C_8$-alkylene or a group

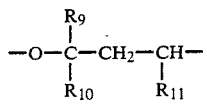

in which $R_9$, $R_{10}$, $R_{11}$ independently of one another are each $C_1$-$C_4$-alkyl, or A, if n is 2, is a group of the formula IV

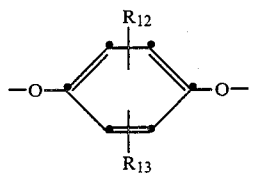

in which $R_{12}$ and $R_{13}$, independently of one another, are each $C_1$-$C_{18}$-alkyl or a group of the formula III or A is a group of the formula V

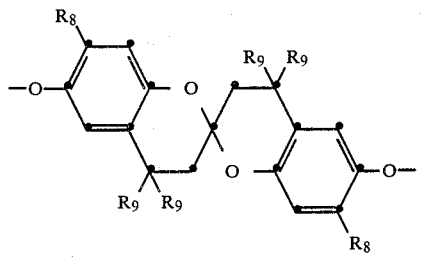

in which $R_8$ and $R_9$ are as defined above.

3. A process according to claim 1, wherein the compound used has the formula I in which A, if n is 1, is a group of the formula II in which $R_1$ and $R_2$, independently of each other, are each hydrogen, $C_1$-$C_{18}$-alkyl or $C_7$-$C_{21}$-aralkyl, and $R_3$ is hydrogen, or $R_2$ and $R_3$ together are $C_2$-$C_8$-alkylene, or A, if n is 2, is a group of the formula IV in which $R_{12}$ and $R_{13}$ are each $C_1$-$C_{18}$-alkyl or a —X—C(O)$OR_4$ group in which X and $R_4$ are as defined in claim 1.

4. A process according to claim 1, wherein the compound used has the formula I in which A, if n is 1, is a group of the formula VI

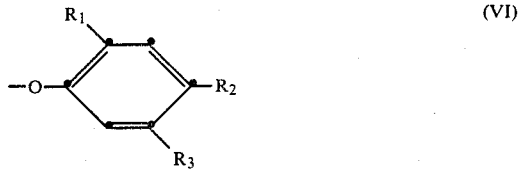

in which $R_1$ and $R_2$ are each branched $C_4$-$C_8$-alkyl or α,α-dimethylbenzyl and $R_3$ is hydrogen, or $R_2$ and $R_3$ together are the —$C(CH_3)_2$—$CH_2$—$C(CH_3)_2$— group, or A, if n is 2, is a group of the formula VII

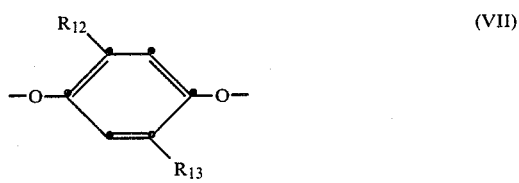

in which $R_{12}$ and $R_{13}$ are each branched alkyl or a group of the formula VIII

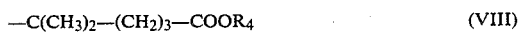

—$C(CH_3)_2$—$(CH_2)_3$—$COOR_4$ (VIII)

in which $R_4$ is straight-chain $C_1$-$C_{18}$-alkyl.

5. A process according to claim 1, wherein the compound used has the formula I in which A, if n is 1, is a group of the formula VI in which $R_1$ and $R_2$ are each tert.-butyl, 1,1,3,3-tetramethylbutyl or α,α-dimethylbenzyl and $R_3$ is hydrogen or $R_2$ and $R_3$ together are a —$C(CH_3)_2$—$CH_2$—$C(CH_3)_2$— group, or A, if n is 2, is a group of the formula VII in which $R_{12}$ and $R_{13}$ are each tert.-butyl, 1,1,3,3-tetramethylbutyl or a group of the formula VIII in which $R_4$ is $C_1$-$C_{10}$-alkyl.

6. A process according to claim 1, wherein the compound of the formula I used has the formula

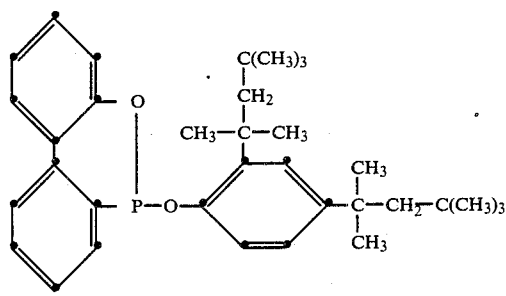

7. A process according to claim 1, wherein the compound of the formula I used has the formula 8. A process according to claim 1, wherein the compound of the formula I used has the formula

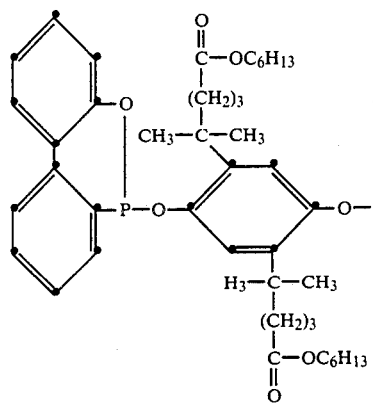

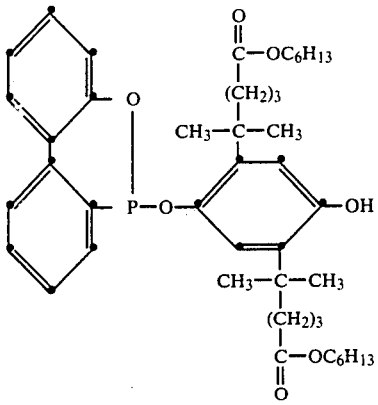

9. A process according to claim 1, wherein the compound of the formula I is used in an amount of 1–400 mol %, based on the magenta coupler.

10. A process according to claim 1, where the photographic material contains at least one further organic stabiliser, UV absorber, fluorescent brightening agents, anti-fogging agent and/or plasticiser.

11. A process according to claim 1, wherein the photographic material contains at least one further colour coupler.

* * * * *